United States Patent [19]

Ross et al.

[11] Patent Number: 4,675,396

[45] Date of Patent: Jun. 23, 1987

[54] 7-OXO-4-THIA-1-AZABICYCLO(3,2,0)HEPTANE DERIVATIVES

[75] Inventors: Barry C. Ross, Luton, England; Graham Johnson, Ann Arbor, Mich.

[73] Assignee: Hoechst UK Limited, Hounslow, England

[21] Appl. No.: 798,858

[22] Filed: Nov. 18, 1985

Related U.S. Application Data

[62] Division of Ser. No. 478,473, Mar. 24, 1983, abandoned.

[30] Foreign Application Priority Data

Mar. 26, 1983 [GB] United Kingdom ................ 8208983

[51] Int. Cl.⁴ .................. C07D 499/00; A61K 31/425
[52] U.S. Cl. .................................................. 540/310
[58] Field of Search ................ 260/245.2 R; 540/310

[56] References Cited

U.S. PATENT DOCUMENTS 4,474,793  10/1984  Ross et al. .................. 260/245.2 R

FOREIGN PATENT DOCUMENTS 24832   3/1981  European Pat. Off. .
80162   6/1983  European Pat. Off. .
99059   1/1984  European Pat. Off. .
110280  6/1984  European Pat. Off. .

OTHER PUBLICATIONS

Chemical Abstracts, vol. 96, No. 25 p. 717 Jun. 1982, Abstract No. 217,577k.

*Primary Examiner*—Nicholas S. Rizzo
*Attorney, Agent, or Firm*—Finnegan, Henderson, Farabow, Garrett & Dunner

[57] ABSTRACT

Compounds of the formula Ia and their tautomers Ib

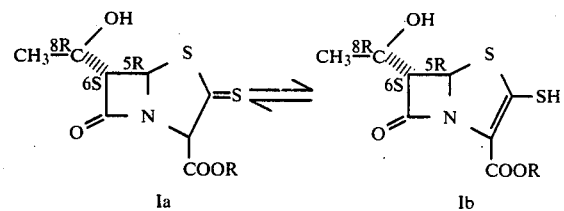

in which formulae R represents a carboxyl esterifying group are described, as well as processes for their manufacture. Ia and Ib are valuable starting materials for the preparation of various derivatives substituted at position 3 that possess antibacterial properties.

9 Claims, No Drawings

7-OXO-4-THIA-1-AZABICYCLO(3,2,0)HEPTANE DERIVATIVES

This is a division of application Ser. No. 478,473, filed Mar. 24, 1983, now abandoned.

The present invention relates to certain intermediates for the preparation of 7-oxo-4-thia-1-azabicyclo[3,2,0-]heptane and hept-2-ene derivatives, and to a process for their preparation.

7-Oxo-4-thia-1-azabicyclo[3,2,0]heptane and 7-oxo-4-thia-1-azabicyclo[3,2,0]hept-2-ene penem have the following structures:

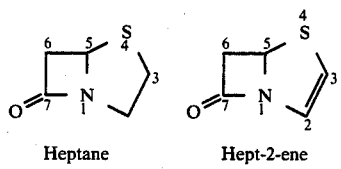

Heptane     Hept-2-ene

Certain derivatives of these basic structures have antibiotic properties, see, for example, British Patent Applications Nos. 2 074 563, 2 042 520 and 2 013 674. There are, however, disadvantages in the methods proposed for synthesising such compounds, for example, the low yields generally achieved, which are exacerbated by the isomeric composition of the product: it is well known that certain stereochemistry in penem compounds is desirable as isomers having this stereochemistry are more biologically active than other isomers. Many of the processes proposed for the production of penem derivatives and their precursors do not give predominantly the desired isomers, and the search continues for more effective methods of synthesising these structures.

The present invention provides a compound of the general formula Ia and its tautomer Ib

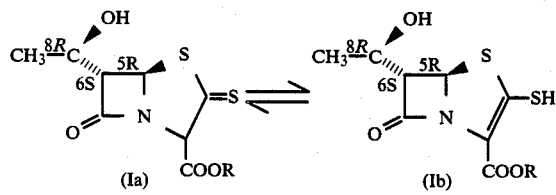

in which formulae R represents a carboxyl esterifying group removable by hydrolysis, photolysis, reduction, or enzyme action to give the free acid.

The term "a compound of the general formula I" and "a ompound of formula I" are both used herein to denote a compound of the general formula Ia, a compound of the general formula Ib, or any mixture thereof. "A compound of formula II" is used to denote collectively compounds of formulae IIa, IIb and IIc. The terms "a compound of formula III" and "a compound of formula IV" are used analogously.

The present invention also provides a process for the production of a compound of the general formula I, which comprises treating a compound of the general formula IIa, IIb, or IIc

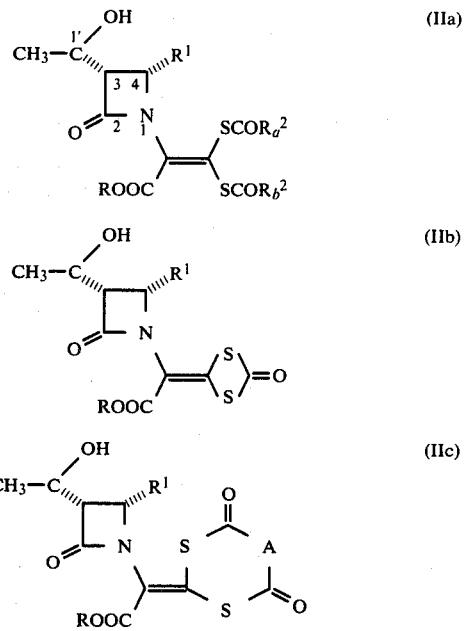

in which R is as defined above, $R^1$ represents a chlorine or bromine atom, the radicals $R_a^2$ and $R_b^2$, which may be the same or different, each represents an alkyl group having from 1 to 4 carbon atoms, especially a methyl or t-butyl group, an aryl group, especially a phenyl group, or an aralkyl group, especially a benzyl group, and A represents a direct bond or the residue of a dicarboxylic acid, with a base.

The base used in the above reaction must be capable of splitting a sulphur-carbonyl bond in the compound of formula II and of bringing about ring closure. The base may be inorganic or organic, for example, ammonia, or an alkali metal (especially a sodium or potassium) carbonate, bicarbonate, or hydroxide; a primary amine, for example, methylamine, ethylamine, aniline or benzylamine; an alkali metal alkoxide, for example, sodium methoxide; or a heterocyclic base, for example, having a $pK_a$ within the range of from 5 to 9, for example, imidazole or pyridine or a substituted pyridine, for example, an alkyl-, amino-, or alkylamino-substituted pyridine, for example, 4-methyl- or 4-dimethylamino-pyridine. Imidazole is particularly preferred.

The reaction is generally carried out in a solvent or diluent, the choice of which is wide, provided that it is inert under the reaction conditions. Examples of solvents and diluents are oxygenated hydrocarbons, for example, alcohols, for example, having up to 4 carbon atoms, for example, methanol and ethanol; ethers, for example, having up to 4 carbon atoms, for example, diethyl ether, also tetrahydrofuran and dioxane; ketones, for example, having up to 4 carbon atoms, for example acetone and methyl ethyl ketone; esters, for example, methyl acetate and ethyl acetate; and amides, for example, dimethylformamide and dimethylacetamide; also chlorinated hydrocarbons, for example, chloroform, methylene chloride and carbon tetrachloride; aromatic hydrocarbons, for example, benzene and toluene; and other solvents, for example, acetonitrile and nitromethane. A mixture of any two or more solvents may be used, and solvents are preferably used in admixture with water, preferably a water-miscible solvent in admixture with 5 to 20% (v/v) water, especially a mixture of dioxane and water, preferably 5 to 10% (v/v) water.

The reaction is generally carried out at a temperature within the range of from 0° to 40° C., preferably from 0° to 20° C.

An esterified carboxyl group —COOR is, for example, an ester formed with an unsubstituted or substituted aliphatic, cycloaliphatic, cycloaliphatic-aliphatic, aryl, araliphatic, heterocyclic or heterocyclic-aliphatic alcohol having up to 20 carbon atoms, or is, for example, a silyl or stannyl ester.

R may represent, for example a straight or branched chain substituted or unsubstituted alkyl, alkenyl or alkynyl group having up to 18 carbon atoms preferably, up to 8 carbon atoms, and especially up to 4 carbon atoms, for example, a methyl, ethyl, n-propyl, iso-propyl, n-butyl, sec-butyl, iso-butyl, tert-butyl, n-pentyl, n-hexyl, allyl, or vinyl group.

An aliphatic group R, especially a methyl group, may be substituted by a cycloalkyl, aryl or heterocyclic group, or R may itself represent a cycloalkyl, aryl or heterocyclic group.

A cycloaliphatic group R may have up to 18 carbon atoms and is, for example, a cyclopentyl, cyclohexyl or adamantyl group. An aryl group may have up to 12 carbon atoms and may have two or more fused rings. An aryl group R is, for example, an unsubstituted or substituted phenyl group, and an unsubstituted or substituted aralkyl group is, for example, a benzyl, p-nitrobenzyl or benzhydryl group.

A heterocyclic group may have one or more heteroatoms, selected from oxygen, nitrogen and sulphur, and up to 14 atoms in total. A heterocyclic group is, for example, an oxygen-containing heterocyclic group, for example, a tetrahydropyranyl or phthalidyl group.

A stannyl group R may have up to 24 carbon atoms, for example, R may represent a stannyl group having three substituents, which may be the same or different, selected from alkyl, alkenyl, cycloalkyl, aryl, aralkyl, alkoxy and aralkoxy groups, for example, alkyl groups having up to 4 carbon atoms, for example, n-butyl groups, phenyl and benzyl groups, especially three n-butyl groups.

A silyl group R may also have up to 24 carbon atoms and three substituents, which may be the same or different, selected from alkyl, alkenyl, cycloalkyl, aryl and aralkyl groups, for example alkyl groups having up to 4 carbon atoms, for example, methyl and t-butyl groups.

Any group R that is capable of substitution may be substituted, for example, with a halogen atom, especially a chlorine or bromine atom, or a nitro group.

The group R may be removable by hydrolysis, by photolysis, by reduction or by enzyme action to give the free acid, or two or more methods may be used, for example, reduction followed by hydrolysis. A group R that may be removed readily without substantial degradation of the rest of the molecule is particularly useful as a carboxyl protecting group. Examples of esters that are readily split by reduction are arylmethyl esters, for example, benzyl, p-nitrobenzyl, benzhydryl and trityl esters.

A stannyl ester, for example, a tri-n-butyl stannyl ester, may be split readily by hydrolysis, for example, by solvolysis, for example, using water, an alcohol, a phenol or a carboxylic acid, for example, acetic acid.

Certain ester groups may be split off by base hydrolysis, for example, acetylmethyl and acetoxymethyl ester groups.

There may be used an esterifying group that is removable under physiological conditions, that is to say, the esterifying group is split off in vivo to give the free acid or the carboxylate, for example, an acyloxymethyl ester, e.g. an acetoxymethyl or pivaloyloxymethyl ester, an aminoalkanyloxymethyl ester, for example, an L-glycyloxymethyl, L-calyloxymethyl or L-leucyloxymethyl ester, or a phthalidyl ester, or an optionally substituted 2-aminoethyl ester, for example, a 2-diethylamino-ethyl or 2-(1-morpholino)-ethyl ester.

Preferred esters are the p-nitrobenzyl, phthalidyl, pivaloyloxymethyl, acetylmethyl and acetoxy-methyl esters.

A compound of the general formula IIa, IIb, or IIc is preferably produced by halogenating a compound of the general formula IIIa, IIIb or IIIc, respectively.

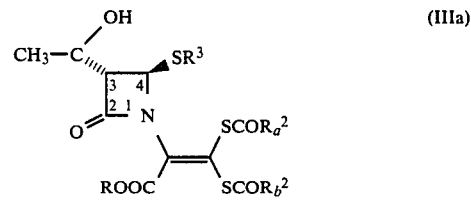

(IIIa)

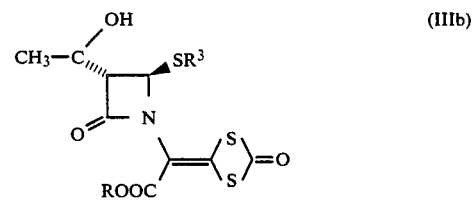

(IIIb)

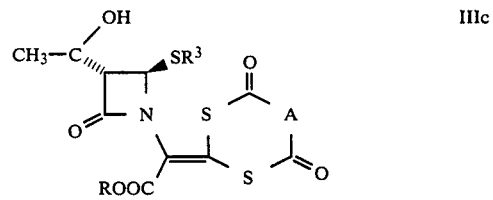

IIIc in which R, $R_a^2$, $R_b^2$ and A are defined as above, and $R^3$ represents an alkyl group having from 1 to 8, preferably from 1 to 6, and especially from 1 to 4 carbon atoms, for example, an ethyl group, or an alkenyl group having up to 6 carbon atoms, especially an allyl group.

The halogenation of a compound of formula IIIa, IIIb or IIIc is carried out with an agent capable of splitting a carbon-sulphur bond and introducing a halogen atom. Such agents are well known in the art and include, for example, molecular chlorine, molecular bromine, sulphuryl chloride, sulphuryl bromide, t-butyl hypochlorite and cyanogen chloride.

The halogenating agent is generally used in an amount of from 1 to 2 mole equivalents, calculated on the compound of formula III. The reaction is generally carried out at a temperature within the range of from −40° to +20° C. The reaction is generally carried out in a solvent or diluent that is aprotic and is inert under the reaction conditions, for example, an ether, a hydrocarbon or a halogenated hydrocarbon, for example, dioxane, benzene, chloroform or methylene chloride. A mixture of two or more solvents may be used. Examples of halogenating systems are: chlorine in chloroform and, especially, chlorine in benzene and t-butyl hypochlorite in benzene. In the latter two cases, the temperature is preferably from 5° to 20° C., and especially from 5° to 10° C.

A compound of formula IIIa, IIIb, or IIIc is preferably produced by removing the protective group from a compound of formula IVa, IVb or IVc, respectively,

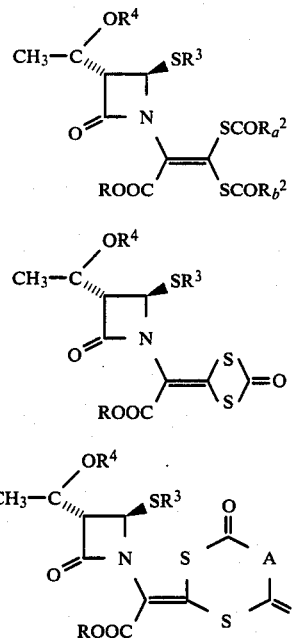

in which R, $R_a^2$, $R_b^2$, $R^3$ and A are defined as above, and $R^4$ denotes a hydroxy protecting group.

Preferred groups $R^4$ are those which are compatible with the synthesis of the compound of formula IV and which may be removed under reaction conditions in which the resulting compound III is stable. Compound III has been found to be stable in the presence of a proton source, for example, hydrogen chloride, aqueous hydrochloric acid or aqueous hydrofluoric acid. Accordingly, one type of preferred hydroxy protecting groups $R^4$ are those which may be removed under acidic conditions. Such groups are well known in the art and are for example, tetrahydropyranyl and tetrahydrofuranyl groups; acetal and ketal groups, for example, of formula

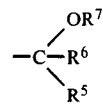

in which $R^6$ and $R^7$, which may be the same or different, each represents a hydrogen atom or a lower alkyl group, preferably a methyl group, or $R^6$ and $R^7$ together with the carbon atom to which they are attached represent a cycloalkyl ring having from 4 to 7 carbon atoms, for example, a tetrahydropyranyl or tetrahydrofuranyl ring; and $R^5$ represents a lower alkyl group, preferably a methyl or ethyl group. $R^4$ may also represent a silyl group, for example, as described above in relation to R, for example, —$SiR^8R^9R^{10}$ groups, in which $R^8$, $R^9$ and $R^{10}$, which may be the same or different, each represents a lower alkyl group or an aryl group, for example, triethylsilyl, t-butyldimethylsilyl and methyldiphenylsilyl groups; and stannyl groups, for example, as described above in relation to R, for example, $SnR^{11}R^{12}R^{13}$ groups, in which $R^{11}$, $R^{12}$ and $R^{13}$, which may be the same or different, each represents a lower alkyl group, for example, a tri-n-butylstannyl group. Preferred $R^4$ groups are tetrahydropyranyl, 2-methoxyprop-2yl and t-butyldimethylsilyl groups.

A t-butyldimethylsilyl group may be removed in a known manner by acid hydrolysis, for example, using moderately concentrated hydrochloric acid, for example 6M HCl, e.g., in tetrahydrofuran (cf Belgian Patent Specification No. 881 012), or hydrogen chloride in tetrahydrofuran, dimethylformamide, dioxane, a lower alkanol, or acetonitrile; Tetra(n-butyl)ammonium fluoride in an acidic medium, e.g., in acetic acid (cf Belgian Patent Specification No. 882 764); or aqueous hydrogen fluoride e.g., in the presence of acetonitrile (cf J. Chem. Soc. Perkin 1, 1981, 2055). (The term 'known' is used herein to mean in actual use in the art or described in the literature of the art).

A compound of the general formula IV may be prepared according to the following reaction scheme:

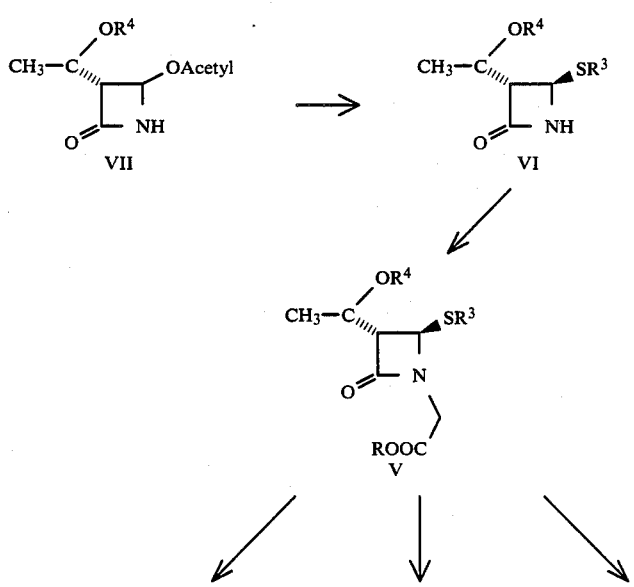

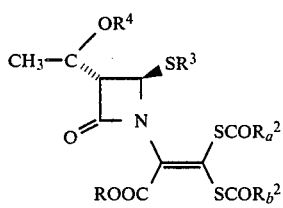 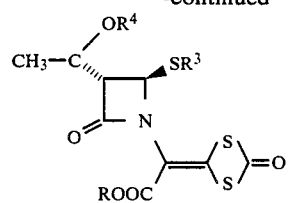 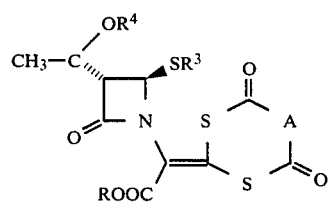

IVa            IVb            IVc in which R, $R_a^2$, $R_b^2$, $R^3$, $R^4$ and A are as defined above.

A compound of formula VII may be prepared as described in Belgian Patent Specification. No. 882 764.

A compound of formula VII may be converted into a compound of formula VI by reaction with a compound of formula VIII $$R^3\text{—}S\text{—}R^{14} \qquad (VIII)$$

in which $R^3$ is as defined above and $R^{14}$ represents a hydrogen atom or an alkali metal atom, especially a sodium or potassium atom. $R^3$ preferably represents a straight chain lower alkyl group, especially an ethyl group, or a straight chain lower alkenyl group, especially an allyl group.

The reaction is generally carried out in a solvent, preferably a protic solvent, for example, water or an alcohol, or an aprotic, water-miscible solvent which is preferably polar, for example, dimethylformamide, dimethyl sulphoxide, tetrahydrofuran or dioxan. The reaction temperature is, for example, from −20° to +50°, preferably from −10° to +20° C.

To obtain a compound of formula V a compound of formula VI may be reacted, in the presence of a base, with a compound of formula IX $$Y^1CH_2CO_2R \qquad (IX)$$

in which R is as defined above and $Y^1$ represents a group that is capable of being replaced by a nucleophilic group and is, for example, a halogen atom, preferably a bromine or iodine atom, or a modified hydroxy group, preferably a sulphonyloxy group of the formula $SO_3R^{16}$ in which $R^{16}$ represents a lower alkyl or —$CF_3$ group, or a phenyl group which is unsubstituted or is substituted by a p-nitro, p-bromo or p-methyl group.

$Y^1$ preferably represents a bromine or iodine atom or a methylsulphonate, trifluoromethylsulphonate, tolylsulphonate or benzenesulphonate group.

The base may be inorganic, organic or organometallic, for example, an alkali metal or alkaline earth metal hydroxide, oxide, carbonate, bicarbonate or hydride, for example, sodium hydroxide, magnesium oxide, potassium carbonate, potassium bicarbonate or sodium hydride; a tertiary amine, for example, a trialkylamine, for example, triethylamine, DABCO (diazabicyclo[2,2,-2]octane), pyridine, or an alkyl-substituted or amino-substituted or dialkylamino-substituted pyridine, for example, N,N-dimethylaminopyridine, or collidine; a guanidine, for example, tetramethylguanidine; DBN (diazabicyclo[4,3,0]non-5-ene) or DBU (diazabicyclo[5,4,0]undec-7-ene), a polymeric base i.e., a base attached to an inert polymeric support e.g., Hunig's base (diisopropylethylamine attached to e.g., polystyrene); a metallated amine, for example, a metallated alkyl- or arylamine, for example, lithium diisopropylamide (LDA), lithium hexamethyldisilazide, lithium piperidide, lithium 2,2,6,6-tetramethylpiperidide, or a Grignard reagent, for example, methylmagnesium bromide. Preferred bases are, for example, potassium carbonate, sodium hydride, lithium diisopropylamide and triethylamine.

The reaction is generally carried out in an aprotic solvent or diluent, for example, a tertiary amide, for example, dimethylformamide, dimethylacetamide or hexamethylphosphoramide; a hydrocarbon, for example, benzene or toluene; or an ether, for example, diethyl ether, tetrahydrofuran or dioxane; or acetonitrile, dimethyl sulphoxide, or sulpholane. Dimethylformamide and dimethylacetamide are preferred. A mixture of two or more solvents and/or diluents may be used.

The reaction may be carried out at a temperature generally within the range of from −80° C. to +30° C. preferably from −40° to +30° C., and especially from −20° to +20° C.

From 1 to 1.5 moles of compound IX are preferably used per mole of compound VI especially from 1 to 1.1 moles of IX per mole of VI. The base is used in an amount, for example, from 1 to 4 moles of base per mole of compound VI.

The reaction is preferably carried out by dissolving compound VI in a solvent, advantageously in dimethylformamide with stirring, adding the base, adding the compound of formula IX and reacting at the desired temperature. The resulting compound of formula V may be worked up and isolated in the usual manner, for example, using chromatographic and/or crystallisation techniques, or the subsequent reaction may be carried out directly on the resulting reaction mixture after removal of any solvent that is not compatible with the subsequent reaction.

If R in formula V represents a carboxyl esterifying group, this group may be converted into another esterifying group R, for example, to introduce a group R that is more easily removable under desired conditions. This transesterification is generally carried out as follows: the ester for formula V is hydrolysed in a known manner unsing, for example, acid or alkaline hydrolysis, preferably using an alkali metal hydroxide, especially sodium or potassium hydroxide. The ester of formula V, for example, a methyl ester, is preferably hydrolysed using an alkali metal hydroxide, especially one mole thereof per mole of the ester of formula V in a solvent, for example ethanol, methanol or water, or an aqueous-organic solvent, for example, tetrahydrofuran/water, ethanol/water, or acetonitrile/water.

The reaction mixture may then be acidified to give a solution of pH 1 to 5, preferably 2 to 4, and the free acid may then be isolated and, if desired, the free acid is then esterified with an esterifying agent capable of introducing a different esterifying group R, for example with an alcohol ROH in the presence of an acid or another activating agent, for example, dicyclohexylcarbodiimide, or with an alkylating agent $RY^1$ in which $Y^1$ is as defined above. Preferably a salt may be isolated and esterified directly.

A compound of formula V may be converted into a compound of formula IV by treatment with a base in the presence of carbon disulphide followed by reaction with an acylating agent, or by treatment with a base, then with carbon disulphide, and finally reaction with an acylating agent. An acylating agent is generally an activated carboxylic acid.

The activated carboxylic acid may be any activated acid derivative comprising the group $R^2$. Such derivatives are well known in the art, and include acid halides, acid anhydrides, and activated esters. An anhydride may be symmetrical or asymmetrical.

For the introduction of a group

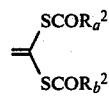

to give a compound of formula IVa, the acylating agent preferably has one of the formulae Xa to Xb

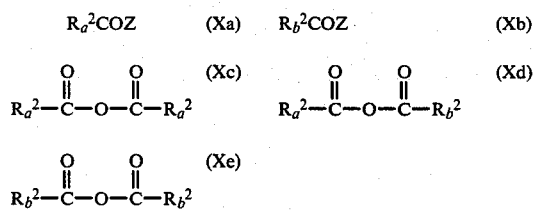

in which $R_a^2$ and $R_b^2$ are as defined above, and Z represents a halogen atom, especially a chlorine or bromine atom or represents an activated ester or amide, or a radical derived from an acid azide. Such coupling reagents are well known in the art of peptide chemistry.

In the case of formula IVb, the group

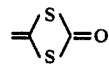

may be introduced by means of an acylating agent of formula XI

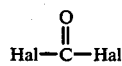

in which Hal represents a halogen atom, especially a chlorine atom.

For the introduction of a group

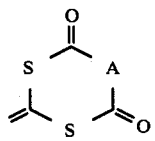

to give a to compound of formula IVc, a dicarboxylic acid derivative of formula XII is used

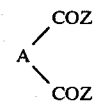

in which A and Z are as defined above, and Z preferably represents a halogen atom, especially a chlorine atom. As mentioned above, A represents the residue of a dicarboxylic acid or represents a direct bond. A is derived, for example, from malonic, dimethylmalonic, succinic, glutaric, adipic, pimelic or phthalic acid.

The compound of formula V is preferably reacted first with a base, then with carbon disulphide, and then finally with the acylating agent.

The base preferably has a pK≧20, and is preferably a metallated amine. Examples of preferred bases are lithium diisopropylamide, lithium 2,2,6,6-tetramethylpiperidide, lithium cyclohexyl isopropylamide, lithium hexamethyl disilazide, and sodamide.

The reaction is generally carried out in an inert solvent, for example, an oxygenated hydrocarbon, preferably an ether, for example, diethyl ether, tetrahydrofuran, dioxane, glyme or diglyme. The reaction temperature is, for example, from −120° to +30° C., preferably from −100° to −20° C.

The amount of base used is for example, from 1 to 4 moles, calculated per mole of compound V, preferably from 2.0 to 3.0 moles of base. Carbon disulphide is preferably used in amount of from 1 to 5 moles, especially from 2 to 3 moles, per mole of compound V.

The reaction is preferably carried out as follows: to a stirred solution of compound V under an inert atmosphere is added the base then carbon disulphide, if desired in solution in the same solvent as compound V or in a different solvent, and finally the acylating agent to complete the reaction.

There may then be admixed a protic source having a pK less than 10 and especially from 5 to 2, for example, acetic, citric, oxalic or formic acid.

The compound of the general formula I has R stereochemistry at position 5. This is the stereochemistry found in naturally occurring penicillins and is, in general, preferable to 5S stereochemistry, more 5R compounds being antibiotically active than are 5S compounds.

We have found a process that gives predominantly the desired 5R compound of formula I. It has been proposed previously (British Patent.Application 2074563A) to halogenate a compound of formula IV i.e., a compound having a protected hydroxy group in the side chain attached to the 3-position, but we have found that this process gives only a 4R halogenated compound, which in its turn, gives a compound analogous to that of formula I but having the undesired 5S stereochemistry. We have found that, very surprisingly, if the protective group is removed from compound IV prior to halogenation, the resulting halogenated compound of formula II is predominantly 4S. The isomer ratio 4S:4R in compound II resulting from the halogenation varies according to the reaction conditions but is, for example, in the range of from 3:1 to as high as 9:1. Moreover, the 4R and 4S isomers of formula II can be separated easily, for example, by chromatography.

The 4S halogenated intermediates of formula II give virtually exclusively a compound of formula I with the 5R stereochemistry as shown. The presumed participation of the free hydroxyl group of the side chain of formula II in giving the more sterically hindered compound of formula I is also unexpected and constitutes a valuable advance in the preparation of the penem compounds of formula I.

The compound of formula I is itself a very useful starting material for the preparation of various derivatives substituted at position 3, especially by —SR$^3$, wherein R$^3$ represents alkyl having 1–10 carbon atoms or substituted alkyl; particularly alkyl having 1–4 C-atoms, i.e., in the synthesis of 3-substituted 7-oxo-4-thia-1-azabicyclo[3,2,0]hept-2-ene 2-carboxylate derivatives, that possess antibacterial properties and which are useful for the treatment of bacterial infections in humans and animals.

The following Examples illustrate the invention. In them, temperatures are given in degrees Celsius.

EXAMPLE 1

4-(R)-Allylthio-3(S)-[1′(R)-{dimethyl-{2-methylprop-2-yl}silyloxy}ethyl]azetidin-2-one To a stirred solution of 1.14 ml of allyl mercaptan and 0.4 g of sodium hydroxide in 25 ml of water under an argon atmosphere was added a solution of 2.87 g of 4-acetoxy-3(S)-[1′-(R)-{dimethyl-{2-methylprop-2-yl}silyloxy}ethyl]azetid-in-2-one in 10 ml of methanol. After 30 minutes, the mixture was partitioned between dichloromethane and water. The separated organic layer was washed with water, was dried over magnesium sulphate, evaporated to dryness, and then chromatographed on silica gel. Elution with ethyl acetate/hexane mixtures afforded 1.8 g of the title compound as white crystals.

$\nu_{(max)}$CDCl$_3$ 3420, 1767 cm$^{-1}$ $\delta$(CDCl$_3$) 0.05 (6H,s), 0.88 (9H, s), 1.20 (3H, d, J6 Hz), 2.9–3.2 (3H, m), 3.9–4.3 (1H, m, H-1′), 3.84 (1H, d J$_{3,4}$ 2 Hz, H-4), 4.95–6.3 (3H, m), 7.28 (1H, broad s)

EXAMPLE 2

Methyl 2-(4(R)-allylthio-3-(S)-[1′(R)-{dimethyl-{2-methylprop-2-yl}silyloxy}ethyl]azetidin-2-on-1-yl) acetate To a stirred solution of 1.76 g of 4(R)-allylthio3-(S)-[1′(R)-{dimethyl-{2-methylprop-2-yl}silyloxy}ethyl]azetidin-2-one in 60 ml of dry dimethylformamide was added 3.52 g of finely ground potassium carbonate and 0.6 ml of methyl bromoacetate. After 18 hours, the mixture was filtered and then partitioned between ethyl acetate and water. The separated organic layer was washed with water and dried over magnesium sulphate. Evaporation in vacuo afforded a crude product which was chromatographed on silica gel. Elution with ethyl acetate/hexane mixtures afforded 1.56 g of the title compound as a pale yellow oil.

$\nu_{max}$CDCl$_3$ 1753, 1768 cm$^{-1}$ $\delta$(CDCl$_3$) 0.06 (6H, s), 0.86 (9H, s), 1.23 (3H, d 6J.5 Hz), 3.2 (3H, m), 3.70 (3H, s), 3.6–4.3 (3H, m), 4.87 (1H, d J 2 Hz, H-4), 4.9–6.3 (3H, m),

EXAMPLE 3

4-Nitrobenzyl 2-(4(R)-allylthio-3(S)-[1′-(R)-{dimethyl-{2-methylprop-2-yl}silyloxy}ethyl]azetidin-2-on-1-yl)acetate To a stirred solution of 3.04 g of potassium hydroxide in 80 ml of 95% ethanol was added a solution of 16 g of methyl 2-(4(R)-allylthio-3(S)-[1′(R)-{dimethyl{2-methylprop-2-yl}silyloxy}ethyl]azetidin-2-on-1-yl)acetate. After 10 minutes, the mixture was evaporated to about 1/5 of its original volume; 2 ml of dimethyl acetamide were added, followed by a solution of 9.25 g of 4-nitrobenzyl bromide in 50 ml of dimethylacetamide. After 1 hour, the mixture was partitioned between 0.01M HCl and ethyl acetate. The separated organic layers were washed with 0.01M HCl, with water, with cold, saturated sodium bicarbonate, and with brine, and were then dried and evaporated. The resulting crude product was chromatographed over silica gel; elution with ethyl acetate/hexane mixtures affored 19.5 g of the title compound as an oil.

$\nu_{max}$(CDCl$_3$) 1755, 1769 cm$^{-1}$ $\delta$(CDCl$_3$) 0.07 and 0.09 (6H, two singlets), 0.88 (9H, s), 1.25 (3H, d J6 Hz), 3.2 (3H, m), 3.7–4.5 (3H, m), 4.95 (1H, d J2 Hz, H-4), 4.9–6.3 (5H, m), 7.5–8.35 (4H, m)

EXAMPLE 4

4-Nitrobenzyl 3,3-di(acetylthio)-[(3S,4R)-4-allylthio 3-[1′(R)-{dimethyl-{2-methylprop-2-yl}silyloxy}ethyl]2-azetidinon-1-yl)propenoate A solution of lithium hexamethyldisilazide was prepared by the addition of n-butyllithium in hexane (2.79 ml of a 1.6M solution) to 0.982 ml of hexamethyldisilazane in 8 ml of dry tetrahydrofuran at −10° C., while stirring under argon. The solution was cooled to −78° C. and added by cannula to a solution of 0.98 g of 4-nitrobenzyl 2-(4(R)-allylthio-3(S)-[1′(R)-{dimethyl-{2-methylprop-2-yl}silyloxy}ethyl]azetidin-2-on-1-yl) acetate in 8 ml of dry tetrahydrofuran at −78° C., with stirring under argon. After 5 minutes, 0.357 ml of carbon disulphide was added by syringe, followed by 0.748 ml of acetic anhydride. The mixture was allowed to warm to room temperature, and 30 ml of dichloromethane was added, followed by 30 ml of water. The organic layer was separated, and the aqueous layer was extracted with further dichloromethane. The combined organic extracts were washed with 1M HCl, with water, and with a 12% sodium chloride solution, and were then dried over magnesium sulphate and evaporated to give 1.38 g of an orange oil. 1.21 g of this crude product was chromatographed on silica gel using ethyl acetate/hexane mixtures as eluent to give 0.800 g of the title compound in purified form.

$\nu_{max}$(CDCl$_3$) 1778, 1745 cm$^{-1}$ $\delta$(CDCl$_3$) 0.06 (6H, s), 0.85 (9H, s), 1.26 (3H, d J6 Hz), 2.25 (3H, s), 2.35 (3H, s), 3.11–3.52 (3H, m, 3-H), 3.35 (2H, d, J 6 Hz), 4.14–4.39 (1H, m), 4.95–6.30 (6H, m), 5.35 (2H, s), 5.56 (1H, d J3 Hz, 4-H), 7.44–8.38 (4H, m)

EXAMPLE 5a

4-Nitrobenzyl 3,3-di(acetylthio)-2-[(3S,4R)-4-allylthio-3-{1′(R)-hydroxyethyl}-2-azetidinon-1-yl]propenoate To a solution of 0.601 g of 4-nitrobenzyl 3,3-di-(acetylthio)-2-[(3S,4R)-4-allylthio-3-(1′(R)-{dimethyl-{2-methylprop-2-yl}silyloxy}ethyl)-2-azetidinon-1-yl]propenoate in 12 ml tetrahydrofuran was added a solution of 1 ml of concentrated hydrochloric acid and 1 ml of tetrahydrofuran. The solution was set aside for 24 hours and then evaporated in vacuo. Benzene was added and the mixture was evaporated to remove residual water to give 0.424 g of crude title product. A portion (0.197 g) of this crude material was chromatographed on silica gel eluting with ethyl acetate-hexane mixtures to give 0.142 g of pure title compound.

max 1774, 1738 cm$^{-1}$ (CDCl$_3$) 1.26 (3H, d, J6 Hz), 2.24 (3H, s), 2.38 (3H, s), 3.35 (2H, d, J7 Hz), 3.22–3.48 (3H, m), 3.98–4.45 (1H, m), 5.30 (2H, s), 4.95–6.1 (6H, m), 7.42–8.23 (4H, m)

EXAMPLE 5b

4-Nitrobenzyl 3,3-di(acetylthio)-2-[(3S,4R)-4-allylthio-3-{1'(R)-hydroxyethyl}-2-azetidinon-1-yl]propenoate To a stirred solution of 0.088 g of 4-nitrobenzyl 3,3-di-(acetylthio)-2-[(3S,4R)-4-allylthio-3-(1'(R)-{dimethyl-{2-methylprop-2-yl}(silyloxy}ethyl)-2-azetidinon-1-yl]propenoate in 5 ml of acetonitrile was added 2.35 ml of concentrated (40%) hydrofluoric acid. A further volume of acetonitrile (5 ml) was added after 5 minutes, and the solution was quenched with a saturated aqueous sodium bicarbonate solution. The resulting solution was extracted with dichloromethane. The resulting organic phase was washed with water, with sodium bicarbonate, and then with brine. It was then dried over MgSO$_4$ and chromatographed on silica gel, eluting with ethyl acetate-hexane mixtures to give 0.03 g of recovered starting material and then 0.0296 g of the title compound.

For spectral details see Example 5a.

EXAMPLE 5c

4-Nitrobenzyl 3,3-di(acetylthio)-2-[(3S,4R)-4-allylthio-3-{1'(R)-hydroxyethyl}-2-azetidinon-1-yl]propenoate To a solution of 5.58 g of 4-nitrobenzyl 3,3-di-(acetylthio)-2-[(3S,4R)-4-allylthio-3-(1'(R)-{dimethyl-{2-methylprop-2-yl}silyloxy}ethyl)-2-azetidinon-1-yl]propenoate in 6.5 ml of tetrahydrofuran was added a freshly prepared solution of 3.72 g of hydrogen chloride in 32 ml of tetrahydrofuran.

The solution was set aside at room temperature until the reaction was complete, and was then evaporated in vacuo. Chromatography on silica gel, eluting with ethyl acetate-hexane mixtures gave 3.10 g of the title compound.

For spectral details see Example 5a.

EXAMPLE 6a

4-Nitrobenzyl 3,3-di(acetylthio)-2-[(3S,4S)-4-chloro-3-{1'(R)-hydroxyethyl}-2-azetidinon-1-yl]propenoate To a solution of 0.246 g of 4-nitrobenzyl 3,3-di-(acetylthio)-2-[(3S,4R)-4-allylthio-3-(1'(R)-hydroxyethyl)-2-azetidinon-1-yl]propenoate in 13 ml of benzene was added under an inert atmosphere 0.095 ml of t-butylhypochlorite. When the starting material had been consumed the reaction mixture was chromatographed on silica gel to give as the minor product 0.045 g of 4-nitrobenzyl 3,3-di-(acetylthio)-2-[(3S,4R)-4-chloro-3-(1'(R)-hydroxyethyl)-2-azetidinon-1-yl]propenoate (20%) and as the major product 0.121 g of the title compound.

For spectral details see Example 13a.

EXAMPLE 6b

4-Nitrobenzyl 3,3-di(acetylthio)-2-[(3S,4S)-4-chloro-3-{1'(R)-hydroxyethyl}-2-azetidinon-1-yl]propenoate To a solution of 3.10 g of 4-nitrobenzyl 3,3-di-(acetylthio)-2-[(3S,4R)-4-allylthio-3-(1'(R)-hydroxyethyl)-2-azetidinon-1-yl]propenoate in 70 ml of dry benzene cooled to 6° was added dropwise a solution of 1.5 mol equivalent of chlorine in 9.5 ml of carbon tetrachloride. When the starting material had been consumed, the solution was reduced in volume in vacuo and chromatographed on silica gel, eluting with ethyl acetate-hexane mixtures to give as the minor product 0.695 g of 4-nitrobenzyl 3,3-di-(acetylthio)-2-[(3S,4R)-4-chloro-3-(1(R)-hydroxyethyl)-2-azetidinon-1-yl]propenoate, and as the major product 1.808 g of the title compound.

For spectral details see Example 13a.

EXAMPLE 7

4-Nitrobenzyl (5R,6S) 6-{8'(R)-hydroxyethy}-7-oxo-4-thia-3-thioxo-1-azabicyclo[3,2,o]hept-2-ane 2-carboxylate To a solution of 0.525 g of 4-nitrobenzyl 3,3-di-(acetylthio)-2-[(3S,4S)-4-chloro-3-(1'(R)-hydroxyethyl)- 2-azetidinon-1-yl]propenoate in 15 ml of dioxan and 1.5 ml of water was added 0.227 g of imidazole. When the reaction was complete the solution was diluted with ethyl acetate and water, acidified with dilute hydrochloric acid and extracted. The aqueous phase was extracted with a second volume of ethyl acetate. The combined ethyl acetate solution was washed with water and then with brine, dried over MgSO$_4$ and evaporated in vacuo to give the title compound as an orange solid in quantitative yield.

$\nu$max (liquid film) 1791, 1751 cm$^{-1}$ $\delta$(CDCl$_3$) 1.39 (3H, d, J6 Hz), 3.00 (1H, s), 3.76 (1H, 2d, J$_{6\beta}$,

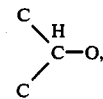

4 Hz, J$_{6\beta,5\alpha}$2 Hz,6-H), 4.05–4.53 (1H, m), 5.35 (2H, s), 5.45 (1H,s), 5.95 (1H, d, 5-H), 7.36–8.45 (4H, m).

EXAMPLE 8

3(S)-{1'(R)-Dimethyl(2-methylprop-2-yl)silyloxyethyl}-4 (R)-ethylthioazetidin-2-one To a stirred solution of 2.03 g of sodium hydroxide in 70 ml of water at 0° C. under an argon atmosphere was added 3.94 g of ethanol thiol. After 30 minutes stirring, a solution of 12.6 g of 3(S)-{1'(R)-dimethyl(2-methylprop-2-yl)silyloxy-ethyl}-4-acetoxyazetidin-2-one in 200 ml of methanol was added. The mixture was warmed to room temperature and, after 90 minutes, was partitioned between ethyl acetate and water. The aqueous layer was further washed with ethyl acetate. The combined organic layers were back-washed with brine, dried over sodium sulphate, and evaporated to dryness. 6.9 g of the title product were obtained. Yield: 54%

$\nu$max (CDCl$_3$) 1765 cm$^{-1}$ $\delta$(CDCl$_3$) 0.10 (6H,s), 0.90 (9H, s), 1.26 (3H, d, J=6 Hz), 1.33 (3H, t, J=7 Hz), 2.68 (2H, q, J=7 Hz), 3.16 (1H, m), 4.1–4.3 (1H, m), 4.85 (1H, d, J=2 Hz), 6.78 (1H, broad s).

EXAMPLE 9

Methyl 2-[3(S)-{1'(R)-(dimethyl(2-methylprop-2-yl)silyloxyethyl}-4(R)-ethylthio-azetidin-2-on-1-yl]acetate To a stirred solution of 6.9 g of 3(S)-{1'(R)-dimethyl(2-methylprop-2-yl)silyloxyethyl}-4(R)-ethylthioazetidin-2-one in 150 ml of dry dimethylformamide was added 13.15 g of finely ground anhydrous potassium carbonate and 2.82 ml of methyl bromoacetate. After 24 hours, the mixture was filtered and then partitioned between ethyl acetate and water. The aqueous layer was adjusted to pH 2 by dropwise addition of dilute hydrochloric acid, and then back-extracted with ethyl acetate. The combined organic layers were washed with water, dried over sodium sulphate, and evaporated in vacuo to give an orange oil, which was chromatographed over silica gel. Elution with ethyl acetate/hexane mixtures afforded 6.37 g of the title compound as a pale yellow oil. Yield: 72%.

max (CDCl$_3$) 1749 (ester) and 1760 ($\beta$-lactam) cm$^{-1}$
(CDCl$_3$) 0.06 (6H, s), 0.86 (9H, s), 1.3 (6H, m), 2.58 (2H, q) J=6 Hz), 3.12 (1H, dd, J=2 Hz and 4 Hz), 3.70 (3H, s), 3.93 (2H, dd, J gem=17 Hz), 4.3 (1H, m), 4.92 (1H, d, J=2 Hz).

EXAMPLE 10

4-Nitrobenzyl 2-[3-(S)-{1'(R)-dimethyl-(2-methylprop-2-yl)-silyloxyethyl}-4(R)-ethylthio-azetidin-2-on-1-yl]acetate To a solution of 6.37 g of methyl 2-[3(S)-{1'(R)-dimethyl(2-methylprop-2-yl)silyloxyethy}-4(R)-ethylthio-azetidin-2-on-1-yl]acetate in 25 ml of 95% ethanol was added a solution of 1.16 g of potassium hydroxide in 25 ml of 95% ethanol. After 15 minutes, the mixture was evaporated in vacuo to dryness. The product was dissolved immediately in 25 ml of dimethylacetamide, and 4.24 g of solid 4-nitrobenzyl bromide were added with vigorous stirring. After 60 minutes, the mixture was partitioned between ethyl acetate and water. The separated aqueous layer was washed with further ethyl acetate; the combined organic layers were backwashed with water, then with brine, and were then dried over sodium sulphate and evaporated in vacuo to afford an orange oil. Chromatography over silica gel, eluting with ethyl acetate/hexane mixtures afforded the title compound as a pale yellow, viscous oil. Yield: 6.18 g, 80%.

$\nu$max (CDCl$_3$) 1765 ($\beta$-lactam) and 1755 (ester)cm$^{-1}$
$\delta$(CDCl$_3$) 0.05 (3H, s), 0.08 (3H, s), 0.88 (9H, s), 1.25 (3H, t, J=7 Hz), 1.28 (3H, d, J=6 Hz), 2.58 (2H, q, J=7 Hz), 3.18 (1H, dd, J=2 Hz and 4 Hz) 4.05 (2H, dd, Jgem=18 Hz), 4.1-4.3 (1H, m), 4.93 (1H, d, J=2 Hz),

EXAMPLE 11

4-Nitrobenzyl 3,3-di(acetylthio)-2-[(3S,4R)-4-ethylthio-3-(1'(R)-{dimethyl-{2-methylprop-2-yl}silyloxy}ethyl)-2-azetidinon-1-yl]propenoate A solution of 2.0 g of 4-nitrobenzyl 2-[3S,4R)-4-ethylthio-3-(1'(R)-{dimethyl-{2-methylprop-2-yl}silyloxy}ethyl)-2-azetidinon-1-yl]acetate in 30 ml of dry tetrahydrofuran was held under an inert atmosphere and cooled to −78°. To the well-stirred solution was added a cooled (−78° C.) preformed solution of lithium hexamethyldisilazide (prepared by addition of butyl lithium (1.55 molar, 6.01 ml, 9.31 mmol) to a tetrahydrofuran solution (20 ml) of hexamethyldisilazane (2.05 ml) cooled to −10°). After 5 minutes, 0.747 ml of carbon disulphide was added, followed after a further 5 minutes stirring by 1.56 ml of acetic anhydride, and the solution was warmed to −20°. 80 ml of ethyl acetate was added to the solution, followed by 150 ml of dilute hydrochloric acid (0.4 molar). The aqueous layer was extracted with a further volume of ethyl acetate. The combined ethyl acetate phase was washed with brine, then dried over magnesium sulphate and evaporated in vacuo to yield 3.03 g of the title compound, which was used subsequently without further purification.

$\nu$max (CDCl$_3$) 1776, 1739, 1715 cm$^{-1}$
$\delta$(CDCl$_3$) 0.06 (6H, s), 0.85 (9H, s), 1.06-1.64 (6H, m), 2.10-3.16(8H, m) 2.23 (3H, s), 2.35 (3H, s), 3.25-3.50 (1H, m, 3-H), 4.05-4.67 (1H, m), 5.34 (2H, s), 5.56 (1H, d, J$_{4\alpha,3\beta}$3 Hz, 4-H), 7.37-8.44 (4H, m).

EXAMPLE 12

4-Nitrobenzyl 3,3-di(acetylthio)-2-[(3S,4R)-4-ethylthio-3-{1'(R)-hydroxyethyl}-2-azetidinon-1-yl]propenoate 0.303 g of 4-nitrobenzyl 3,3-di(acetylthio)-2-[(3S,4R)-4-ethylthio-3-(1'(R)-{dimethyl-{2-methylprop-2-yl}-silyloxy}ethyl)-2-azetidinon-1-yl]propenoate was dissolved in a solution of 12 mol equivalent of hydrogen chloride in 5 ml of tetrahydrofuran. The solution was stirred for 6 hours then evaporated in vacuo to ⅓ of its volume. Ethanol-free chloroform was added and the solution evaporated. The residue was chromatographed on silica gel eluting with ethyl acetate-hexane mixtures to give 0.066 g of recovered starting material and 0.12 g of the title compound.

$\nu$(max) 1770, 1738 cm$^{-1}$
$\delta$(CDCl$_3$) 1.03-1.63 (6H, m), 2.00-3.18 (9H, m), 3.19-3.48 (1H, m, 3-H), 3.95-4.46 (1H, m), 5.30 (2H, s), 5.43 (1H, d, J$_{4\alpha,3\beta}$, 3 Hz, 4-H), 7.33-8.37 (4H, m).

EXAMPLE 13a

4-Nitrobenzyl 3,3-di(acetylthio)-2-[(3S,4S)-4-chloro-3-{1'(R)-hydroxyethyl}-2-azetidinon-1-yl]propenoate A solution of 0.10 g of 4-nitrobenzyl 3,3-di(acetylthio)-2-[(3S,4R)-4-ethylthio-3-{1'(R)-hydroxyethyl}-2-azetidinon-1-yl]propenoate in 1.3 ml of ethanol-free chloroform was cooled to −60° under an inert atmosphere. To this solution was added a solution of chlorine in carbon tetrachloride until the starting material had been consumed. The reaction was evaporated in vacuo and chromatographed on silica gel to give 0.032 g of the title compound.

$\nu$max (liquid film) 1790, 1739 cm$^{-1}$
$\delta$(CDC$_3$) 1.37 (3H, d, J7 Hz), 2.24 (3H, s), 2.39 (3H, s), 3.58 (1H, 2d, J$_{3\beta}$, O—CH—CH$_3$10 Hz, J$_{3\beta,4\beta}$5 Hz, 3-H), 4.00-4.56 (1H, m), 5.30 (2H, s), 6.27 (1H, c, 4-H), 7.38-8.25 (4H, m).

EXAMPLE 13b

4-Nitrobenzyl 3,3-di(acetylthio)-2-[(3S,4S) 4-chloro-3-[1'(R)-hydroxyethyl-2-azetidinon-1-yl]propenoate To a solution of 0.10 g of 4-nitrobenzyl 3,3-di-(acetylthio)-2-[(3S,4R) 4-ethylthio-3-[1'(R)-hydroxyethyl-2-azetidinon-1-yl]propenoate in 2 ml of dry benzeneI cooled to 6° was added slowly a solution of 1.5 mole equivalent of chlorine in carbon tetrachloride until the starting material had been consumed. The solution was then chromatographed on silica gel, eluting with ethyl acetate-hexane mixtures to give as a minor product 0.011 g of 4-nitrobenzyl 3,3-di(acetylthio)-2-[(3S,4R) 4-chloro-3-(1'(R)-hydroxyethyl)-2-azetidinon-1-yl]propenoate, then as the major product, 0.065 g of the title compound.

For spectral details see Example 13a.

EXAMPLE 14

4-Nitrobenzyl 3,3-di(acetylthio)-2-[(3S,4R)-4-chloro-3-(1'(R)-{dimethyl-{2-methylprop-2-yl}silyloxy}ethyl)-2-azetidinon-1-yl]propenoate A stirred solution of 3.519 g of 4-nitrobenzyl-3,3-di(acetylthio)-2-[(3S,4R)-4-allylthio-3-(1'(R)-{dimethyl-{2-methylprop-2-yl}silyloxy}ethyl)-2-azetidinon-1-yl]-propenoate in 20 ml of ethanol-free chloroform was cooled to −60°. To it was added a solution of 0.48 g of chlorine in 5.6 ml of carbon tetrachloride. The resulting solution was maintained at −60° for 20 minutes, and was then warmed to room temperature, evaporated in vacuo and chromatographed on silica gel to yield 2.32 g of the title compound. mp 145°–146° (from ethylacetate/hexane)

$\nu$max (CDCl$_3$) 1795, 1743 cm$^{-1}$ $\delta$(CDCl$_3$) 0.06 (6H, s), 0.85 (9H, s), 1.31 (3H, d, J6 Hz), 2.25 (3H, s), 2.40 (3H, s), 3.53 (1H, 2d, J$_{3\beta,4\alpha}$2 Hz, J$_{3\beta,SiOCH}$ 3 Hz, 3-H), 4.08–4.50 (1H, m) 5.37 (2H,s), 6.28 (1H, d, 4-H), 7.45–8.42 (4H, m)

EXAMPLE 15

4-Nitrobenzyl(5S,6S) 6-(8(R)-{dimethyl-{2-methylprop-2-yl}silyloxy}ethyl)-7-oxo-4-thia-3-thioxo-1-azabicyclo[3,2,0]hept-2-ane-2-carboxylate To a stirred solution of 0.741 g of 4-nitrobenzyl 3,3-di(acetylthio)-2-[(3S,4R)4-chloro-3-(1(R)-{dimethyl-{2-methylprop-2-yl}silyloxv}ethyl-2-azetidinon-1-yl]propenoate in 20 ml of dioxan and 2 ml of water was added 0.247 g of imidazole. After 20 minutes the solution was diluted with 120 ml of ethyl acetate and extracted with dilute hydrochloric acid, followed by brine. The organic phase was dried over MgSO$_4$ and evaporated in vacuo to give the title compound in quantitative yield.

$\nu$max (liquid film) 1793, 1755 cm$^{-1}$
$\delta$(CDCl$_3$) 0.11 (6H, s), 0.89 (9H, s), 1.41 (3H, d, J6 Hz), 3.96 (1H, 2d, J$_{6\beta SiOCH}$ 4Hz, J$_{6\beta,6\beta}$9 Hz, 6-H), 4.13–4.63 (1H, m), 5.25–5.48 (3H, m), 5.36 (2H, s), 6.05 (1H, d, 5-H), 7.37–8.45 (4H, m)

EXAMPLE 16

4-Nitrobenzyl 5(R),3-ethylthio-6-(S)-{8(R)-hydroxyethyl}-7-oxo-4-thia-1-azabicyclo[3,2,0]hept-2-ene 2-carboxylate To a stirred solution of 0.188 g of 4-nitrobenzyl (5R,6S)-{1'(R)-hydroxyethyl}-7-oxo-4-thia-3-thioxo-1-azabicyclo[3,2,0]heptane 2-carboxylate in 10 ml of dry tetrahydrofuran was added 0.094 ml of ethyl diisopropylamine followed by 0.119 ml of iodoethane. When the reaction was shown to be complete (by means of thin layer chromatography) the solvent was removed in vacuo and the residue chromatographed on 10 g of silica gel (eluting with ethyl acetate-hexane) to give 0.14 g of the title compound.

EXAMPLE 17

Potassium 5(R), 3-ethylthio-6(S)-{8(R)-hydroxyethyl-}7-oxo-4-thia-1-azabicyclo[3,2,0]hept-2-ene 2-carboxylate To a solution of 0.139 g of 4-nitrobenzyl 5(R), 3-ethylthio-6(S)-{1(R)-hydroxyethyl}-7-oxo-4-thia-1-azabicyclo[3,2,0]hept-2-ene 2-carboxylate 15 ml of ethyl acetate was added 15 ml of an aqueous solution of 0.034 g of potassium bicarbonate followed by 0.28 g of palladium on charcoal. The mixture was hydrogenated at 50 psi for one hour then filtered through 'HYFLO' which is a trade mark for a filtration aid. The aqueous phase was extracted once with 10 ml of fresh ethyl acetate and then hydrolysed to give 0.06 g of the title compound.

EXAMPLE 18

4-Nitrobenzyl 2-(4(R)-ethylthio-3(S)-[1'(R)-dimethyl[2-methylprop-2-yl]silyloxyethyl]-2-azetidinon-1-yl)-2-(4-oxo-1,3-dithietan-2-ylidene)acetate A solution of lithium hexamethyldisilazide was prepared by the addition of n-butyllithium in hexane (4.21 ml of a 1.6M solution) to 2.13 ml of hexamethyldisilazane in 10 ml of dry tetrahydrofuran at 0° C. while stirring under nitrogen. The solution was added via a cannula to a solution of 1.08 g of 4-nitrobenzyl 2-(4(R)-ethylthio-3(S)-[1'(R)-dimethyl-{2-methylprop-2-yl}silyloxyethyl]-2-azetidinon-1-yl)acetate in 10 ml of dry tetrahydrofuran at −78° C., with stirring under nitrogen. After 5 minutes, 0.35 ml of carbon disulphide was added by syringe and after a further 90 minutes phosgene in toluene (3.56 ml of a 12.5% solution) was added by syringe. The mixture was stirred for 90 minutes and poured into 50 ml of diethyl ether and 10 ml of 2M acetic acid. The organic layer was separated, washed with water, 12% sodium chloride solution, dried over magnesium sulphate and evaporated to give an orange oil. Chromatography over silica gel using diethyl ether/hexane mixtures as eluent gave 0.485 g of the title compound in purified form.

$\nu$max (CDCl$_3$) 1770, 1760 cm$^{-1}$
$\delta$(CDCl$_3$) 0.04 (6H, s), 0.81 (9H, s), 1.18 (3H, T, J=7 Hz), 1.22 (3H, d, J=7 Hz), 2.51 (2H, q, J=7 Hz), 3.18 (1H, dd, J=2.7 and 3.7 Hz), 4.24 (1H, dq, J=2.7 and 7 Hz), 5.31 (1H, d, J 32 2.7 Hz), 5.23, 5.45 (2H, AB, J=13 Hz), 7.55, 8.23 (2H, A$_2$B$_2$, J=9 Hz)

EXAMPLE 19

4-Nitrobenzyl-2-(4(R)-ethylthio-3(S)-[1'(R)-hydroxyethyl]-2-azetidinon-1-yl)-2-(4-oxo-1,3-dithietan-2-ylidene)acetate 0.30 g of 4-Nitrobenzyl 2-(4(R)-ethylthio-3(S)-[1(R)-dimethyl{2-methylprop-2-yl}silyloxyethyl]-2-azetidinon-1-yl)-2-(4-oxo-1,3-dithietan-2-ylidene)acetate was dissolved in 4 ml of dry DMF containing a trace of para-quinol under a nitrogen atmosphere protected from light. The solution was treated with 5 mol equivalent of hydrogen chloride in 2.2 ml of DMF. The solution was stirred for 4 hours and diluted with 5 ml of water, poured into 20 ml of diethyl ether and the organic layer separated. The aqueous portion was re-extracted with a further volume of diethyl ether and the organic fractions combined washed with water, dried over magnesium sulphate and evaporated to give a yellow oil. Chromatography over silica gel using diethyl ether/hexane mixtures as eluant gave 0.21 g of the title compound in purified form.

$\nu$max (CDCl$_3$) 34 50, 1785, 1760 cm$^{-1}$,
$\delta$(CDCl$_3$) 1.13 (3H, t, J=7 Hz), 1.18 (3H, d, J=7 Hz), 2.39 (1H, br s), 2.51 (2H, q, J=7 Hz), 3.17 (1H, dd, J=2.7 and 3.3 Hz), 4.22 (1H, m), 5.24 (1H, d, J=2.7 Hz), 5.29 (2H, s), 7.52, 8.17 (2H, A$_2$B$_2$, J=9 Hz)

EXAMPLE 20

4-Nitrobenzyl 2-(4(S)-chloro-3(S)-[1'(R)-hydroxyethyl]2-azetidinon-1-yl)-2-(4-oxo-1,3-dithietan-2-ylidene)acetate A solution of 0.208 g of 4-nitrobenzyl 2-(4(R)-ethylthio-3(S)-[1'(R)-hydroxyethyl]-2-azetidinon-1-yl)-2-(4-oxo-1,3-dithietan-2-ylidene)acetate in 1 ml of ethanolfree chloroform was cooled to −30° C. under a nitrogen atmosphere and treated with 1.1 mol equivalent of chlorine in 0.82 ml of carbon tetrachloride. The reaction mixture was permitted to warm to room temperature and the solvent evaporated in vacuo. Chromatography on silica gel using diethyl ether/hexane mixtures as eluant gave 0.015 g of 4-nitrobenzyl 2-(4(R)-chloro-3(S)-[1(R)-hydroxyethyl]-2-azetidinon-1-yl-2-(4-oxo-1,3-dithietan-2-ylidene)acetate and 0.03 g of the title compound.

$\nu_{max}$ (CDCl$_3$) 1775 cm$^{-1}$.

δ(CDCl$_3$) 1.45 (3H, d, J=6.3 Hz), 3.59 (1H, dd, J=4.4 and 9.3 Hz), 4.37 (1H, m), 5.33, 5.40 (2H, AB, J=13 Hz), 6.08 (1H, d, J=4.4 Hz), 7.53, 8.27 (4H, A$_2$B$_2$J=8.6 Hz),

EXAMPLE 21

4-Nitrobenzyl (5R, 6S) 6-(8(R)-hydroxyethyl)-7-oxo-4-thia-3-thioxo-1-azabicyclo[3,2,0]hept-2-ane-2-carboxylate To a solution of 0.028 g 4-nitrobenzyl 2-(4(S)-chloro-3(S)-[1'(R)-hydroxyethyl]-2-azetidinon-1-yl-2-(4-oxo-1,3-dithietan-2-ylidene)acetate in 1 ml of 10% aqueous dioxane at 5° C. was added a trace of imidazole. When the reaction was complete the solution was diluted with diethyl ether and water, acidified with dilute hydrochloric acid and extracted. The aqueous phase was extracted with a second volume of diethyl ether and the organic portions combined, washed with water, 12% sodium chloride solution, dried over magnesium sulphate and evaporated to give 0.01 g of crude product. Comparison of its NMR spectrum with that of the product of example 7 proved the existence of the title compound in the product mixture.

What is claimed is:

1. A process for the production of a compound of the formula Ia or Ib wherein

R means a carboxyl esterifying group removable by hydrolysis, photolysis, reduction, or enzyme action to give the free acid characterized in that (a) a compound of the formula IIIa, IIIb or IIIc in which R is as defined above R$_a^2$ and R$_b^2$, which may be the same or different, each represents an alkyl group having from 1 to 4 carbon atoms, a phenyl group, and A represents a direct bond or the residue of a dicarboxylic acid, and R$^3$ represents an alkyl group having from 1 to 8 carbon atoms, or an alkenyl group having up to 6 carbon atoms, is halogenated to give a compound of formula IIa, IIb or IIc in which R, R$_a^2$, R$_b^2$ and A are as defined above and R$^1$ represents a chlorine or bromine atom, and that (b) this compound of formula IIa, IIb or IIc is treated with a base.

2. A process according to claim 1 characterized in that $R^3$ represents an ethyl or allyl group.

3. A process according to claim 2, characterized in that the compound of formula IIIa, IIIb or IIIc is halogenated with molecular chlorine, molecular bromine, sulphuryl chloride, sulphuryl bromide, t-butyl hypochlorite or cyanogen chloride.

4. A process according to claim 1 characterized in that a compound of formula IIa, IIb or IIc in which $R_a^2$ and $R_b^2$ each represents a methyl group is treated with a base.

5. A process according to claim 1 characterized in that a compound of formula IIa, IIb or IIc in which $R_a^2$ and $R_b^2$ each represents a t-butyl group is treated with a base.

6. A process according to claim 1 characterized in that a compound of formula IIa, IIb or IIc in which $R_a^2$ and $R_b^2$ each represents a phenyl group is treated with a base.

7. A process according to claim 1 characterized in that the base is ammonia, an alkali metal carbonate, bicarbonate or hydroxide wherein the alkali metal is sodium or potassium, a heterocyclic base, or a primary alkyl amine wherein the alkyl group has 1 to 8 carbon atoms.

8. A process according to claim 7 characterized in that the heterocyclic base has a pKa within the range of from 5 to 9.

9. A process according to claim 7 characterized in that the heterocyclic base is imidazole.

* * * * *